United States Patent [19]

Pages

[11] Patent Number: 5,514,070
[45] Date of Patent: May 7, 1996

[54] PLURAL COLLECTOR CENTRIFUGE BOWL FOR BLOOD PROCESSING

[75] Inventor: Etienne Pages, Saint Avertin, France

[73] Assignee: Haemonetics Corporation, Braintree, Mass.

[21] Appl. No.: 184,677

[22] Filed: Jan. 21, 1994

[51] Int. Cl.⁶ .................................................... B04B 7/08
[52] U.S. Cl. ............................................... 494/41; 494/64
[58] Field of Search ............................ 494/38, 41, 44, 494/43, 64, 65, 76

[56] References Cited

U.S. PATENT DOCUMENTS

| | | | |
|---|---|---|---|
| 3,145,713 | 8/1964 | Latham, Jr. | 494/41 X |
| 3,409,213 | 11/1968 | Latham, Jr. | 494/41 |
| 3,565,330 | 2/1971 | Latham, Jr. | 494/41 |
| 4,140,268 | 2/1979 | Lacour | 494/41 |
| 4,300,717 | 11/1981 | Latham, Jr. | 494/65 X |
| 4,416,654 | 11/1983 | Schoendorfer et al. | 494/10 |
| 4,464,167 | 8/1984 | Schoendorfer et al. | |
| 4,684,361 | 8/1987 | Feldman et al. | 494/41 |
| 4,692,136 | 9/1987 | Feldman et al. | 494/38 |
| 4,767,396 | 8/1988 | Powers | 494/60 |
| 4,859,333 | 8/1989 | Panzini . | |
| 4,879,031 | 11/1989 | Panzani | 494/38 X |
| 4,943,273 | 7/1990 | Pages | 494/41 |
| 4,983,158 | 1/1991 | Headley | 494/41 |
| 5,045,048 | 9/1991 | Kaleskas et al. | 494/41 |
| 5,100,372 | 3/1992 | Headley | 494/41 |
| 5,387,174 | 2/1995 | Rochat | 494/41 X |

FOREIGN PATENT DOCUMENTS 0285891  10/1988  European Pat. Off. .

OTHER PUBLICATIONS

Invention Disclosure, "Harvest Bowl Design", Headley et al., Apr. 3, 1992, pp. 1–4.

*Primary Examiner*—David Scherbel
*Assistant Examiner*—Charles E. Cooley
*Attorney, Agent, or Firm*—Cesari and McKenna

[57] ABSTRACT

A centrifuge bowl for separating whole blood into less dense and more dense components and for collecting both less dense and more dense components without stopping bowl rotation. The fluid pathway from an inlet port to a separation chamber comprises an inlet tube and an introduction passageway. The fluid pathway from the separation chamber to an outlet port comprises a collection passageway. The introduction and collection passageways are nonrotatable. The more dense blood components can be extracted from the bowl during rotation by applying suction at the inlet port or pressure at the outlet port.

20 Claims, 2 Drawing Sheets

PLURAL COLLECTOR CENTRIFUGE BOWL FOR BLOOD PROCESSING

BACKGROUND OF THE INVENTION

In 1968 a disposable blood processing bowl was introduced by the inventor, Allen Latham, Jr., in a paper entitled "A New Approach to Automated Centrifugal Processing of Blood" at the 21st Annual Meeting of the American Association of Blood Banks. Mr. Latham described a system for processing blood using an expendable, or disposable, centrifuge rotor in the form of a relatively inexpensive bowl. The system was proposed for use in a number of pheresis procedures, such as plasmapheresis and plateletpheresis. In these processes, whole blood is taken from a donor and various blood components are separated from the whole blood and harvested while some components are returned to the donor. The system was also suggested for use in cell washing, such as in deglycerization, in which thawed deglycerized red cells are washed to remove the glycerine preservative before being infused in a patient.

In operation, the bowl is held in a chuck which is attached to a spindle and driven by a motor. The bowl consists of a rotor, or bowl body portion in which blood component is separated and a stator portion consisting of an input and output port. A rotary seal couples the stator to the rotor. One side of the input port is connected through a first peristaltic pump to a source of whole blood from a donor and the other side is in fluid communication with a fractionation volume in the rotor. Anticoagulant is mixed with the whole blood prior to entry into the centrifuge bowl.

The rotor is rotated at a fixed speed and various blood fractions are collected at the output port and directed into appropriate containers, such as plastic bags, by diverting the flow through plastic tubing in accordance with the setting of three-way clamp/switches.

Fractionation within the centrifuge is determined by the relative densities of the different cell components being separated and collected. The various cell fractions pass through the outlet port of the centrifuge bowl by progressive displacement from the lower portion of the bowl.

The bowl consists of two major components. One is a rotatable bowl body with an inner core mounted coaxial to a central longitudinal axis through the bowl body. The other is a rotary seal and header assembly, which is provided on top of the bowl body.

The bowl body is divided into two chambers, the first is an upper collection chamber adjacent an upper radially extending collection passageway leading to the output port. The second is a separation chamber formed between the longitudinally extending cylindrical wall of the core and the side wall of the bowl body.

Anticoagulated whole blood introduced to the bowl body via the fixed input port is coupled to the bottom of the bowl body by a fixed inlet tube coupled to the input port and extending longitudinally therefrom along a central longitudinal axis to the bottom wall of the bowl body.

Whole blood is coupled to the separation chamber via one or more radially extending introduction passageways formed between an inner surface of the lower bowl body wall and a lower radially extending wall of the core which extends in parallel to the lower bowl body wall leaving a narrow entrance at the extended outer diameter of the bowl for introduction of whole blood from the introduction chamber into the separation chamber.

Separated less dense whole blood component in the separation chamber is coupled to the collection chamber via a passageway formed between radially inwardly extending wall portions of the core and bowl body leading to the upper collector passageway and through the output port. The upper collector passageway is formed by a pair of opposed radially outwardly extending members which lead to a longitudinally extending coaxial passageway coupled to the outlet port.

The header assembly must remain fixed, since the inlet and outlet tubing to, or from, a donor or patient, is coupled to it. The rotary seal provides an appropriate interface between the fixed header and the rotating bowl body.

The system, including the bowl, interconnecting tubing and receptacles, are connected together and sterilized in advance of use, so that they arrive in sterile form ready for immediate use. All parts, other than the rotary seal assembly, are generally made from blood-compatible plastic, such as polycarbonate (for the bowl), or polyethylene (for the tubing and receptacles).

One of the disadvantages of the centrifuge bowls described above is that, when the last of the less dense components, i.e. plasma, platelets, etc., are being displaced by passage through the outlet port, the supply of an anticoagulated whole blood must be interrupted to prevent the outflow of the more dense components, i.e., red blood cells (RBC). The centrifuge is stopped leaving concentrated RBC in the bowl which are then collected by suctioning out through the inlet port prior to commencing another separation cycle.

As noted by Panzani in U.S. Pat. No. 4,859,333 this interruption is particularly disadvantageous in the case of intraoperative autotransfusion where whole blood is washed and RBC separated for rapid reinfusion. Panzani's solution to this problem is to add a third port 12(a) connected to an additional central conduit 12 which extends to the bottom of the bowl and which is sealed from the conventional inlet tubing by a gasket 13. (U.S. Pat. No. 4,859,333 Col. 4, lines 9–20).

A vacuum or negative pressure is applied to the third port where it is desired to collect RBC which are drawn up the additional conduit 12 which is in communication with bottom passage 16, which is in the peripheral communication with outer passage 7 where the concentrated RBC are located (U.S. Pat. No. 4,859,333, Col. 4, lines 42–54).

SUMMARY OF THE INVENTION

In accordance with the present invention an additional passageway is provided at the bottom of the centrifuge bowl to enable collection of the denser fraction (e.g. RBC) of whole blood component separated in the bowl.

This additional passageway is formed by providing a radially outwardly extending communication channel or introduction passageway at the distal end of the fixed inlet tube. This radial extension is formed by upper and lower planar disc-like members which depend from the distal end of the inlet tube and extend outwardly to an introduction chamber formed at the bottom of the bowl. The members extend radially outwardly the same distance as the upper collection passageways in the conventional prior art centrifuge bowl described above.

When desired, more dense blood component can be collected while the bowl is rotating by introducing less dense component fluid or a physiological solution fluid, such as, saline into the conventional output port. Fluid entering the outlet port travels in a reverse direction to the separation chamber which forces more dense component out the separation chamber to the introduction chamber, out the introduction passageway at the distal end of the input tube, and from there out the input port for collection or harvesting.

DETAILED DESCRIPTION OF THE INVENTION

Figure 1:
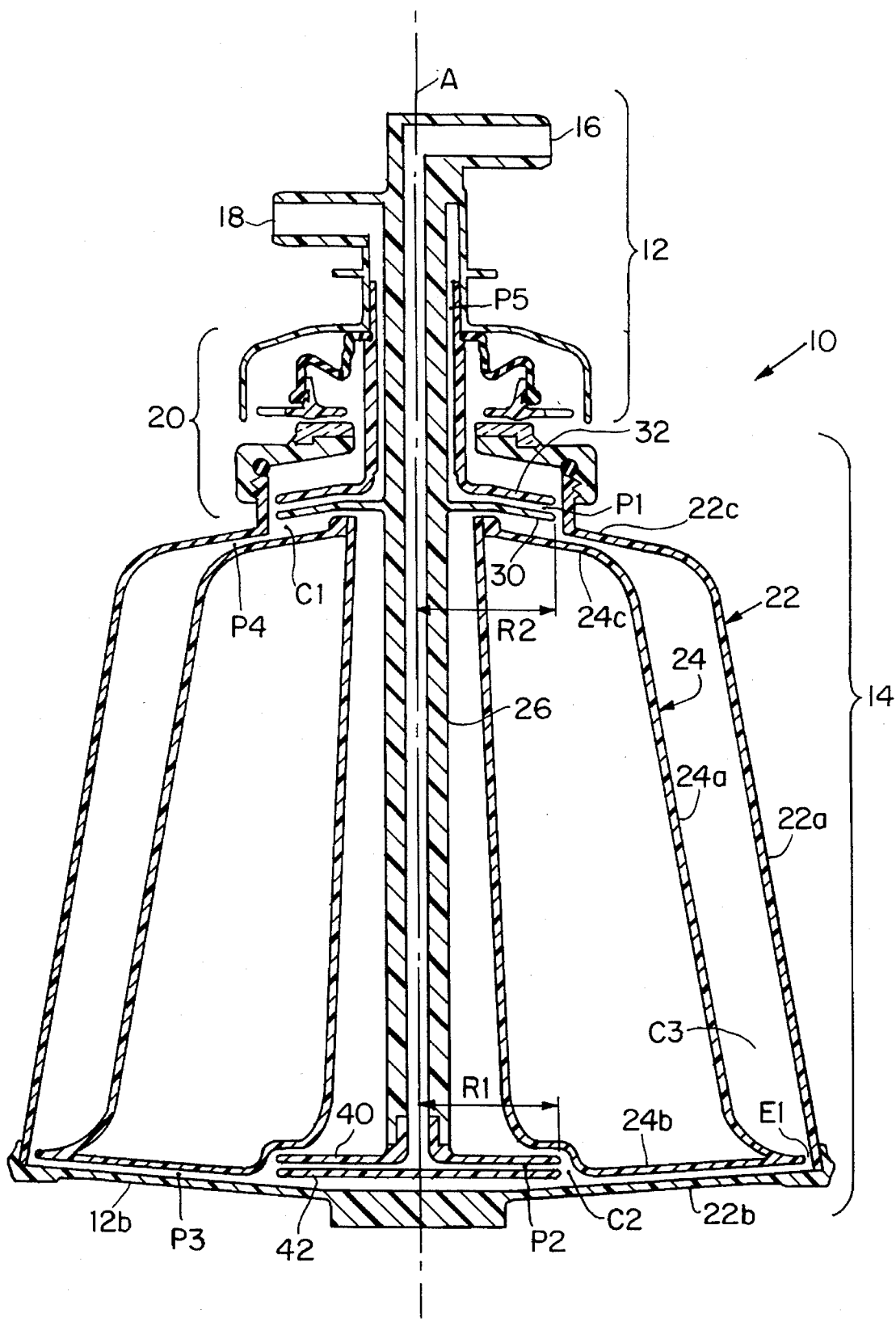
FIG. 1 is a front elevational view in section illustrating the structure of a first embodiment of the invention.

A first embodiment of the invention will now be described in connection with FIG. 1.

The centrifuge bowl is held in a chuck (not shown) which is attached to a spindle and driven by a motor (also not shown). The bowl consists of a rotor, or bowl body portion 14 in which blood component is separated and a stator portion 12 consisting of an input port 16 and output port 18. A rotary seal 20 couples the stator 12 to the rotor 14. One side of the input port is connected through a first peristaltic pump (not shown) to a source of whole blood from a donor and the other side is in fluid communication with a fractionation volume in the rotor 14. Anticoagulant is mixed with the whole blood prior to entry into the centrifuge bowl.

The rotor 14 is rotated at a fixed speed and various blood fractions are collected at the output port 18 and directed into appropriate containers (not shown), such as plastic bags, by diverting the flow through plastic tubing in accordance with the setting of three-way clamp/switches (not shown).

Fractionation within the centrifuge bowl is determined by the relative densities and sizes of the different cell components being separated and collected. The various cell fractions pass through the outlet port 18 of the centrifuge bowl by progressive displacement from the lower portion of the bowl.

The bowl 10 consists of two major components. One is the rotatable bowl body, per se, 22 with an inner conical core 24 mounted coaxial to a central longitudinal axis A through the bowl body. The other is a rotary seal and header assembly 12, which is provided on top of the bowl body 14.

The bowl body 14 is divided into three chambers C1, C2 and C3. The first chamber, C1, is an annular upper collection chamber adjacent an upper radially extending collection passageway P1 leading to the output port 18. The second chamber, C2, is a lower annular introduction chamber adjacent a lower radially extending introduction passageway P2 at the distal end of an inlet tube 26 at the bottom of the bowl. The third chamber, C3, is a separation chamber formed between a tapered longitudinally extending cylindrical wall 24a of the core and a side wall 22a of the bowl body.

Chambers C1 and C2 are interconnected to Chamber C3 by passageways P4 and P3, respectively, formed between bowl body walls and core walls. Anticoagulated whole blood introduced to the bowl body 14 via the fixed input port 16 is coupled to the bottom of the bowl body by the fixed inlet tube 26 which extends along central longitudinal axis A to the lower introduction chamber C2.

Whole blood in the introduction chamber C2 is coupled to the separation chamber C3 via one or more radially extending passageways P3 formed between an inner surface of the lower bowl body wall 22b and a lower radially extending wall 24b of the core which extends in parallel with the lower bowl body wall 22b leaving a narrow entrance E1 at the extended outer diameter of the bowl for introduction of whole blood from the introduction chamber C2 into the separation chamber C3.

Separated less dense whole blood component in the separation chamber C3 is coupled to the collection chamber C1 via passageway P4 formed between radially inwardly extending wall portions 24C and 22C, respectively, of the core and bowl body leading toward the upper collection passageway P1 and thence through the output port 18. The upper collection passageway P1 is formed by a pair of opposed radially outwardly extending and inclined members 30, 32 which lead to a longitudinally extending coaxial passageway P5 coupled to the outlet port 18.

Preferably, the centrifuge system, including the bowl 10, interconnecting tubing and receptacles, are connected together and sterilized in advance of use, so that they arrive in sterile form ready for immediate use. All parts, other than the rotary seal assembly, are generally made from blood-compatible plastic, such as polycarbonate (for the bowl), or polyethylene (for the tubing and receptacles).

In accordance with the present invention introduction passageway P2 provided at the bottom of the centrifuge bowl, in conjunction with the adjacent introduction chamber C2, enables collection of the denser fraction (e.g. RBC) of whole blood component separated in chamber C3.

This additional introduction passageway P2 is formed by providing a radially outwardly extended communication channel or extension at the distal end of the fixed inlet tube. This radial extension is formed by upper and lower planar disc-like members 40 and 42 which depend from the distal end of the inlet tube 26 and extend outwardly the same radial distance R1 as the radial extension R2 of the upper collection passageway P1 in the conventional prior art centrifuge bowl described above.

When desired, the more dense blood component, such as RBC, can be collected while the bowl is rotating by introducing the less dense component fluid, such as, plasma or a physiological solution fluid, such as, saline into the conventional output port 18. Fluid entering the outlet port 18 travels in a reverse direction down coaxial collection passageway P5, through radial passageway P1, through collection chamber C1, radial passageway P4 and into the separation chamber C3; which forces the more dense component out of separation chamber C3 through radial passageway P3 to the introduction chamber C2. From C2, the fluid passes out the additional introduction passageway P2 at the distal end of the input tube 26 and from there out the input port 16 for collection or harvesting.

Figure 2:
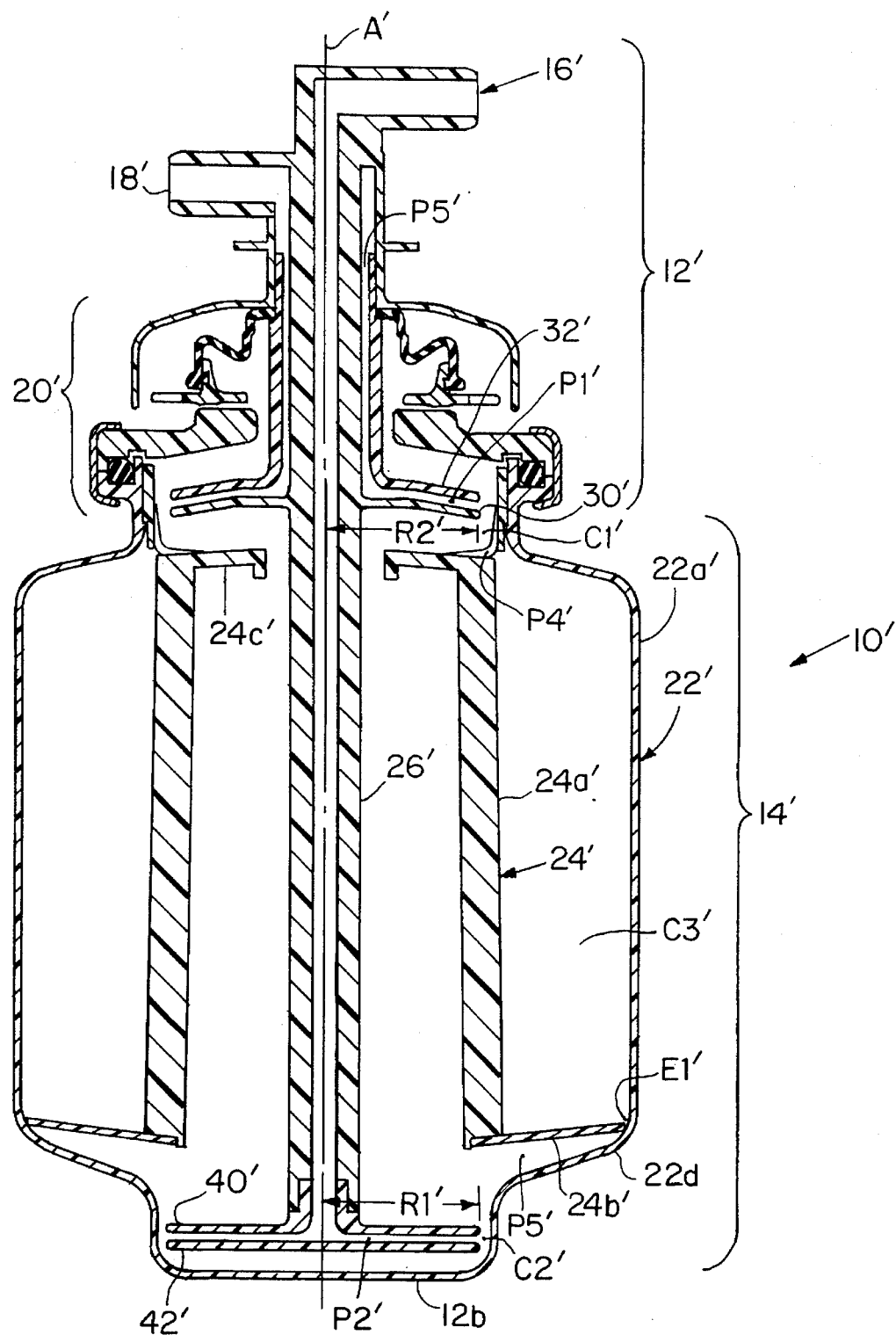
FIG. 2 is a front elevational view of a second embodiment of the invention.

In the alternate embodiment of FIG. 2 like parts carry the same reference numbers with a prime suffix. In view of the general similarity between FIGS. 1 and 2 only the differences will be described in detail.

The general bowl configuration in FIG. 2 is similar to the bowl shown in U.S. Pat. No. 4,943,273 issued Jul. 24, 1990 (and incorporated herein by reference). Whereas the FIG. 1 bell-shaped bowl configuration is similar to that described in U.S. Pat. No. 5,045,048 issued Sep. 3, 1991 (also incorporated herein by reference).

The main differences are as follows:

In the FIG. 2 bowl, the core 24' is formed of a thick molded cylindrical longitudinally extending side wall 24a' and upper and lower radially extending walls 24c' and 24b', respectively.

Lower wall 24b' extends radially outwardly from wall 24a' and upper wall 24c' extends radially inwardly from wall 24a'. The introduction chamber C2' is located at the outlet of introduction passageway P2' and is coupled to separation chamber C3' via passageway P5' formed between core wall 24b' and radially outward inclined bowl wall 22d.

Separation chamber C3' is coupled to collection chamber C1' by passageway P4' formed in upwardly extending circular core wall.

As in FIG. 1, the radial extensions R1' and R2' of introduction and collection passageways P2' and P1', respectively, are made equal to allow reverse flow of fluid through the chambers while the bowl is spinning.

This completes the description of preferred embodiments of the invention.

Possible applications for the invention include:

a) Plasma collection, in which the extra corporeal volume (ECV) is minimized along with platelet contamination.
   When the prior art bowls are used for plasmaphereses, several centrifuge collection cycles are required to collect about 600 ml. of plasma. This is because the bowl volume is less than the volume of RBC's associated with 600 ml. of plasma. As a consequence the "buffy coat," which is composed of platelets and white cells, reaches the collection chamber C1 several times, thereby contaminating the plasma exiting the bowl.
   By way of contrast, in the present invention RBC's can be removed before the layer of platelets reaches the collection chamber C1, thereby minimizing contamination of the plasma and allowing a smaller bowl to be used without multiplying the number of centrifuge braking collection cycles.

b) Platelet or leukocyte collection in which ECV is minimized while allowing Buffy Coat growth.
   With the prior art bowl operated in a "surge" protocol and the platelet collection is the result of two steps: the "buffy coat" grows while the bowl is filling, and this buffy coat is elutriated by the surge process from its fixed position in the bowl to the effluent line through the collection chamber. The limitations of the platelet collection (White blood cell contamination, platelet efficiency) is in the buffy coat size at the moment of the surge. This buffy coat size is itself limited by the volume processed per cycle.
   The new bowl allows one to process more whole blood, even with a smaller bowl volume, to grow a single "buffy coat".

c) Cell saving in which high hematocrit washed RBC can be pumped out, whatever the volume processed, so that one bowl volume design can be used for all cell washing applications.

d) RBC collection, in which the contamination with platelets and white blood cells could be minimized. After the plasma collection has been done, the RBC's could be collected without disturbing the "buffy coat" by introducing preservative solution into the bowl.

Equivalents

Those skilled in the art will know, or be able to ascertain using no more than routine experimentation, many equivalents to the specific embodiments of the invention described herein. For example, the difference between the so called cell collection and the introduction chambers C1 and C2 respectively is not in the function of collecting or introducing blood product from or into the separation chamber. The difference is in the fact that the collection chamber C1 allows the collection of separated components from the less dense to the more dense, and that the introduction chamber C2 allows the converse.

Another way to differentiate the collection chamber C1 from the introduction chamber C2 is that the entrance/exit E1 from/to passageway P5 is at the maximum radius of the separation chamber C3 while the entrance/exit from/to passageway P4 is at the minimum radius of the separation chamber C3.

Also note that the volumes of the C1 and C2 chambers should be small (an order of 1/10) compared to the volume of the separation chamber C3.

These and all other equivalents are intended to be encompassed by the following claims.

What is claimed is:

1. A blood processing centrifuge bowl for separating whole blood into more dense and less dense components comprising:
   (a) a bowl body rotatable about a longitudinal axis and having:
      (i) an upper wall radially extending from said axis and having an aperture therethrough;
      (ii) a lower wall radially extending from said axis; and
      (iii) a side wall joining the upper and lower walls;
   (b) a nonrotatabLe assembly comprising an inlet port, an outlet port, and an inlet tube extending longitudinally from the inlet port;
   (c) a rotary seal assembly joining the nonrotatable assembly and the bowl body such that the inlet tube extends into the bowl body through the aperture;
   (d) a hollow core, within and joined to the bowl body so as to facilitate rotation therewith, the core having a side wall and being coaxial to the longitudinal axis of the bowl body;
   (e) a separation chamber defined by the side wall of the bowl body and the side wall of the core;
   (f) a collection passageway disposed above the separation chamber, extending radially from the longitudinal axis and fluidly coupling the separation chamber to the outlet port;
   (g) an introduction passageway disposed below the separation chamber, extending radially from the longitudinal axis and fluidly coupling the separation chamber to the inlet tube; and
   (h) means for preventing the introduction passageway from rotating with the bowl body.

2. The centrifuge bowl of claim 1 wherein the collection passageway is defined by opposed upper and lower members.

3. The bowl of claim 2 wherein the opposed members are physically joined to the inlet tube, thereby providing the means for preventing rotation of the introduction passageway.

4. The bowl of claim 2 wherein the members are inclined.

5. The centrifuge bowl of claim 1 wherein the side wall of the bowl body and the side wall of the core are generally parallel.

6. The bowl of claim 1 wherein the side wall of the bowl body is generally conical.

7. The bowl of claim 1 wherein the side wall of the bowl body is generally cylindrical.

8. The centrifuge bowl of claim 7 wherein the side wall of the bowl body includes a lower inclined portion where the lower wall of the bowl body joins the side wall of the bowl body.

9. The bowl of claim 1 further comprising a longitudinal passageway, coaxial to the longitudinal axis of the bowl body, for fluidly coupling the outlet port to the collection passageway.

10. The bowl of claim 1 wherein the collection passageway has a distal end and further comprising a collection chamber located adjacent to the distal end of the collection passageway.

11. The bowl of claim 10 wherein the collection chamber is smaller in volume than the separation chamber.

12. The bowl of claim 11 wherein the collection chamber and separation chamber have volumes, the volume of the collection chamber being an order of 10% of the volume of the separation chamber.

13. The bowl of claim 1 wherein the introduction passageway has a distal end and further comprising an introduction chamber located adjacent to the distal end of the introduction passageway.

14. The bowl of claim 13 wherein the introduction chamber is smaller in volume than the separation chamber.

15. The bowl of claim 14 wherein the introduction chamber and separation chamber have volumes, the volume of the introduction chamber being on an order of 10% of the volume of the separation chamber.

16. The centrifuge bowl of claim 13 wherein the introduction passageway is disposed proximal to the joining between the lower wall of the bowl body and side wall of the bowl body.

17. The centrifuge bowl of claim 1 wherein the introduction passageway is defined by opposed upper and lower members.

18. The centrifuge bowl of claim 17 wherein:

(a) the inlet tube comprises a longitudinal bore therethrough and terminates in a distal end;

(b) the upper member of the introduction passageway comprises an aperture therethrough; and (c) the upper member of the introduction passageway is affixed to the distal end of the inlet tube such that the aperture through the upper member is fluidly coupled to the bore of the inlet tube.

19. The centrifuge bowl of claim 1 wherein the collection and introduction passageways are each defined by opposed upper and lower members.

20. The centrifuge bowl of claim 19 wherein the members defining the collection passageway and the members defining the introduction passageway each have radial extents, said extents being equal to one another.

* * * * *